United States Patent
Ashur-Fabian et al.

(10) Patent No.: US 10,398,789 B2
(45) Date of Patent: *Sep. 3, 2019

(54) METHODS, COMPOSITIONS AND KITS FOR PROVIDING A THERAPEUTIC TREATMENT

(71) Applicants: Osnat Ashur-Fabian, Zur Moshe (IL); Aleck Hercbergs, Beachwood, OH (US)

(72) Inventors: Osnat Ashur-Fabian, Zur Moshe (IL); Aleck Hercbergs, Beachwood, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/484,691

(22) Filed: Apr. 11, 2017

(65) Prior Publication Data

US 2017/0274104 A1 Sep. 28, 2017

Related U.S. Application Data

(63) Continuation of application No. 13/643,907, filed as application No. PCT/IL2011/000346 on Apr. 28, 2011, now Pat. No. 9,655,984.

(60) Provisional application No. 61/328,825, filed on Apr. 28, 2010.

(51) Int. Cl.

| | |
|---|---|
| *A61K 51/00* | (2006.01) |
| *A61K 31/195* | (2006.01) |
| *A61K 45/06* | (2006.01) |
| *A61K 31/4164* | (2006.01) |
| *A61K 31/513* | (2006.01) |
| *A61K 31/198* | (2006.01) |

(52) U.S. Cl.
CPC ............ *A61K 51/00* (2013.01); *A61K 31/195* (2013.01); *A61K 31/198* (2013.01); *A61K 31/4164* (2013.01); *A61K 31/513* (2013.01); *A61K 45/06* (2013.01)

(58) Field of Classification Search
CPC ...... A61K 31/195; A61K 45/06; A61K 51/00; A61K 31/4164; A61K 31/513; A61K 2300/00

See application file for complete search history.

(56) References Cited

U.S. PATENT DOCUMENTS

| 6,017,958 A | 1/2000 | Kun et al. |
|---|---|---|
| 2003/0109690 A1 | 6/2003 | Ruben et al. |
| 2003/0185872 A1* | 10/2003 | Kochinke .................. A61F 2/02 424/426 |

FOREIGN PATENT DOCUMENTS

JP 63079824 A 4/1988

OTHER PUBLICATIONS

Singer et al.,Treatment Guidelines for Patients With Hyperthyroidism and Hypothyroidism, JAMA, Mar. 8, 1995, pp. 808-813, vol. 273, No. 10, United States.
Joffe et al., Treatment of Clinical Hypothyroidism With Thyroxine and Triiodothyronine: A Literature Review and Metaanalysis, Psychosomatics 2007, pp. 379-384, vol. 48, United States.
Russsell T. Joffe and Stephen T.H. Sokolov, Thyroid hormone treatment of primary unipolar depression: a review, International Journal of Neuropsychopharmacology, 2000, pp. 143-147,vol. 3, CINP, United Kingdom.
Ofer Agid and Bernard Lerer, Algorithm-based treatment of major depression in an outpatient clinic: clinical correlates of response to a specific serotonin reuptake inhibitor and to triiodothyronine augmentation, International Journal of Neuropsychopharmacology, 2003 ,pp. 41-49, vol. 6, CINP, United Kingdom.
Cooper Kazaz et al.,Combined Treatment With Sertraline and Liothyronine in Major Depression, ARCH GEN Psychiatry, 2007, pp. 679-688, vol. 64, No. 8, American Medical Association, United States .
Jody Ginsberg, Diagnosis and management of Graves' disease, 2003, pp. 575-585, vol. 168, No. 5. Canadian Medical Association, Canada.
Aleck Hercbergs and John T. Leith, Spontaneous Remission of Metastatic Lung Cancer Following Myxedema Coma—an Apoptosis-Related Phenomenon?, Journal of the National Cancer Institute, Aug. 18, 1993, pp. 1342-1343 vol. 85, No. 16, United States.
Hellevik, Al et al., Population Study Thyroid Function and Cancer Risk: A Prospective, Cancer Epidemiol Biomarkers Prevention, 2009, pp. 570-574, vol. 18 No. 2, American Association for Cancer Research, United States.
Manjula S. Kumar et al., Enhancing Effect of Thyroxine on Tumor Growth and Metastases in Syngeneic Mouse Tumor Systems, Cancer Research, 1979, pp. 3515-3518, vol. 39, No. 2, American Association for Cancer Research, United States.
Rosenberg et al., Relationship of Thyroid Disease to Renal Cell Carcinoma, Urology, pp. 492-498, vol. 35, No. 6, United States.
Nelson M. et al., Association Between Development of Hypothyroidism and Improved Survival in Patients With Head and Neck Cancer, Arch Otolaryngol Head Neck Surg. 2006, pp. 1041-1046, vol. 132, No. 10, American Medical Association, United States.
Cristofanilli et al., Thyroid Hormone and Breast Carcinoma Primary Hypothyroidism Is Associated with a Reduced Incidence of Primary Breast Carcinoma, Cancer, 2005, pp. 1122-1128, American Cancer Society, United States.
Theodossiou et al., Propylthiouracil-Induced Hypothyroidism Reduces Xenograft Tumor Growth in Athymic Nude Mice, Cancer, 1999, pp. 1596-1601, vol. 86, No. 8, American Cancer Society, United States.
Hercberg et al., Propylthiouracil-induced Chemical Hypothyroidism with High-dose Tamoxifen Prolongs Survival in Recurrent High Grade Glioma: A Phase 1/11 Study, Anticancer Research, 2003, pp. 617-626, vol. 23, United States.

(Continued)

*Primary Examiner* — Robert S Cabral
(74) *Attorney, Agent, or Firm* — Browdy and Neimark, PLLC

(57) ABSTRACT

The present invention encompasses a therapeutic method which employs treatment of a disease such as cancer with triiodothyronine (T3) together with an anti-thyroid treatment such as treatment with an anti-thyroid agent, treatment with radioiodine and surgical removal of all or part of the thyroid gland. A pharmaceutical composition comprising T3 and an anti-thyroid agent and a kit comprising the same are also encompassed by the invention.

9 Claims, 5 Drawing Sheets

(56) References Cited

OTHER PUBLICATIONS

Garfield and Hercberg, Fewer Dollars, More Sense, Journal of Clinical Oncology, 2008, pp. 5304-5309, vol. 26, No. 32, American Society of Clinical Oncology, United States.

Desgrosellier et al., Integrins in cancer: biological implications and therapeutic opportunities, Nature Reviews Cancer, 2010, pp. 9-22, vol. 10, Macmillan Publishers Limited., United States.

Davis et al., Acting via a Cell Surface Receptor, Thyroid Hormone Is a Growth Factor for Glioma Cells, Cancer Research, 2006, pp. 7270-7275, vol. 66, No. 14, American Association for Cancer Research, United States.

International Search Report: Application No. PCT/IL 11/00346, European Patent Office, Sep. 12, 2011, Alexandria, Virginia, United States.

Hercbergs et al., Medically Induced Euthyroid Hypothyroxinemia May Extend Survival in Compassionate Need Cancer Patients: An Observational Study, The Oncologist, 20:72-76 (2015).

Ashur-Fabian et al., Long-term response in high-grade optic glioma treated with medically induced hypothyroidism and carboplatin:a case report and review of the literature, Anti-Cancer Drugs, 24(3):315-323 (2013).

Hercbergs et al., Abstract entitled "Medically induced euthyroid hypothyroxinemia may improve outcomes in glioblastoma (GBM) patients—an observational study", oral presentation at The II International Symposium on Clinical and Basic Investigation in Glioblastoma (Toledo GBM Conference), Toledo, Spain, Sep. 9-12, 2015.

Lin et al., L-Thyroxine vs. 3,5,3'-triiodo-L-thyronine and cell proliferation: activation of mitogen-activated protein kinase and phosphatidylinositol 3-kinase, Am J Physiol Cell Physiol, 296:C980-C991 (2009).

Davis et al., Membrane receptor for thyroid hormone: physiologic and pharmacologic implications, Annu Rev Pharmacol Toxicol, 51:99-115 (2011) Abstract.

\* cited by examiner

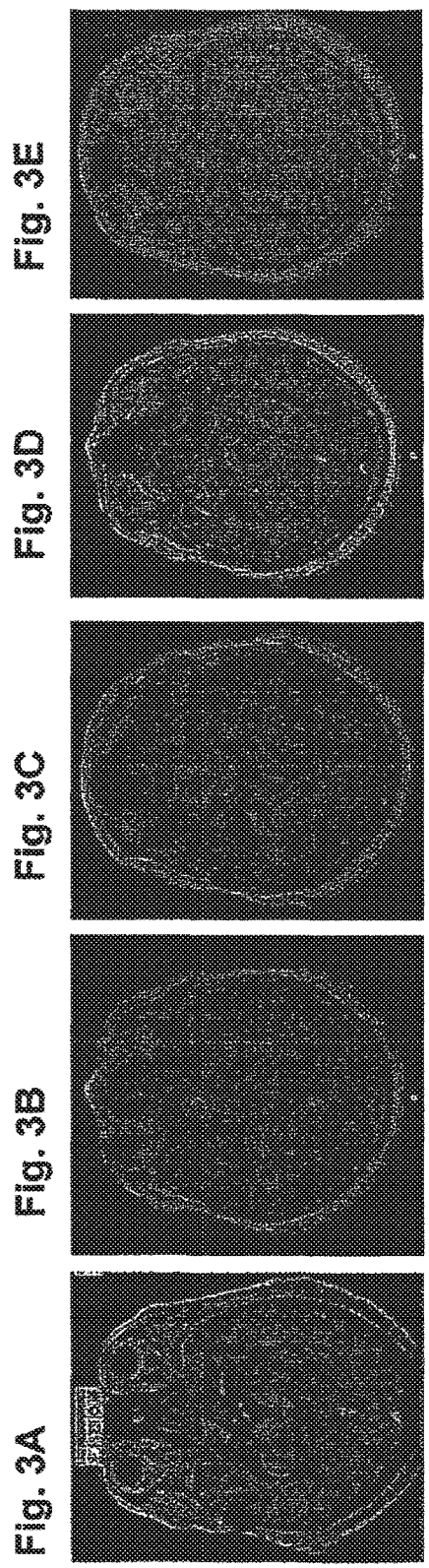

METHODS, COMPOSITIONS AND KITS FOR PROVIDING A THERAPEUTIC TREATMENT

FIELD OF THE INVENTION

The present invention relates in general to therapeutic methods and in particular to methods, compositions and kits for treating cancer.

PRIOR ART

The following is a list of prior art which is considered to be pertinent for describing the state of the art in the field of the invention, some of which is also being discussed below.
[1] Singer P A, at al. *JAMA*. 1995; 8; 273(10):808-12.
[2] Joffe R T and Levitt A J, *Psychosoatics* 2007; 48:5.
[3] Joffe and Sokolov. *Int J Neuropsychopharmacol.* 2000; 3(2):143-147.
[4] Agid and Lerer, *Int J Neuropsychopharmacol.* 2003; 6(1):41-9.
[5] Cooper-Kazaz R, et al. *Arch Gen Psychiatry.* 2007; 64(6):679-88.
[6] Ginsberg J, *CMAJ*. 2003; 4; 168(5):575-85.
[7] Hercbergs and Leith, *J Natl Cancer Inst.* 1993 Aug. 18; 85(16):1342-3.
[8] Hellevik A I, et al. *Cancer Epidemiol Biomarkers Prev.* 2009; 18(2):570-4.
[9] Kumar M S, et al. *Cancer Res.* 1979; 39(9):3515-8.
[10] Rosenberg A G et al. *Urology*. 1990; 35(6):492-8.
[11] Nelson M, et al. *Arch Otolaryngol Head Neck Surg.* 2006; 132(10):1041.6.
[12] Cristofanilli M, et al. *Cancer.* 2005; 15; 103(6):1122-8.
[13] Theodossiou C, et al. *Cancer.* 1999; 86(8): 1596-1601.
[14] U.S. Pat. No. 6,017,958.
[15] Hercbergs A, et al. *Anticancer Research,* 2003; 23:617-626.
[16] Garfield D H and Hercbergs A, *JCO*. 2008; 26(32): 5304-5309.
[17] Japanese patent application No. 63-79824.
[18] Desgrosellier J S, et al. *Nature Reviews Cancer.* 2010; 10: 9-22.
[19] Davis F B, et al. *Cancer Res.* 2006; 66(14):7270-5.

BACKGROUND OF THE INVENTION

The thyroid hormones thyroxine ($T_4$) and triiodothyronine ($T_3$) play a significant role in the growth, development and differentiation of normal cells. Thyroxine (3,5,3',5'-tetraiodothyronine, $T_4$), is the major hormone secreted by the follicular cells of the thyroid gland. Triiodothyronine, ($T_3$) is a thyroid hormone similar to $T_4$ but with one fewer iodine atoms per molecule. Thyroid-stimulating hormone (TSH), secreted from the hypophisis, controls the production of $T_4$ and $T_3$. In the thyroid, $T_4$ is converted to $T_3$, however, most of the circulating $T_3$ is formed peripherally by deiodination of $T_4$ (85%). Thus, $T_4$ acts as prohormone for $T_3$.

$T_4$ is the standard thyroid hormone used for replacement therapy in patients with hypothyroidism [1]. $T_4$ in combination with $T_3$ for treatment of clinical hypothyroidism was reviewed [2]. $T_4$ in combination with $T_3$ or $T_4$ alone have also been used to treat various mood disorders such as unipolar depression [3] and major depression. $T_3$ alone (at daily doses of 25-50 μg for 4 weeks) was found to be effective in treating depression in patients non-responsive to serotonin selective reuptake inhibitors [4]. Further, $T_3$ (20-25 μg per day for 1 week; 40-50 μg/day thereafter) was combined with Sertalin to treat depression [5].

Excess of thyroid hormones (i.e. hyperthyroidism) resulting in an excess of circulating free $T_4$ and $T_3$ or both, which is a mark of Grave's disease, can be treated by using anti-thyroid drugs such as propylthiouracil (PTU) and methimazole [6].

Current research points to a link between the level of thyroid hormone and the risk for developing cancer. Clinical studies, in addition to animal studies have suggested that thyroid hormones may positively modulate neoplastic cells. On the other hand, it was postulated that lowering the levels of thyroid hormones (i.e. by introducing a hypothyroid state) can lead to decreased tumorgenicity and increased survival. For example, Hercbergs and Leith reported on a patient suffering from metastatic lung cancer in which spontaneous remission of his cancer was documented, following a myxedema coma episode (extremely low levels of thyroid hormones) [7].

Hellevik A I et al. showed that TSH levels suggestive of hyperthyroid function were associated with increased risk of cancer [8]. Kumar M S, et al. also showed, using an animal model, that $T_4$ stimulates tumor growth and metastasis [9].

Rosenberg A G et al. suggested an epidemiologic link between thyroid dysfunction and renal cell carcinoma [10].

Nelson M, et al. Reported improved survival in hypothyroid head and neck cancer patients and hypothesized that maintaining patient at a clinically tolerable level of hypothyroidism may have a beneficial effect in regard to their neoplastic disease [11].

Cristofanilli M, et al. pointed to a reduced risk and significantly older age at onset/diagnosis of primary breast carcinoma in patients suffering from primary hypothyroidism [12].

Theodossiou C, et al. indicates that human lung and prostate tumors do not grow well in hypothyroid nude mice. [13].

Mendeleyev J, et al. described a method of treating a malignant tumor using a $T_4$ analogue having no significant hormonal activity [14].

Hercbergs A, et al. describe that propylthiouracil-induced chemical hypothyroidism with high dose tamoxifen prolonged survival in recurrent high grade glioma. [15]. Hercbergs A also found a highly significant correlation between a free thyroxine decline below the reference range and the six month progression free survival [16].

Japanese patent application No. 63-79824 [17] describes carcinostatic agents comprising as active ingredients iodotyrosine, such as monoiodotyrosine (MIT) and diiodotyrosine (DIT); and/or iodothyronine, such as triiodothyronine ($T_3$) and iodothyroxinee ($T_4$). The dosage range described for MIT and DIT is 10 mg to 10 g/day per 50 kg body weight, to be administered by intravenous injection or orally; and with regard to $T_3$ and $T_4$, administration includes IV injection in the range from 1 μg to 1 mg/day per 50 kg body weight, preferably using both in dosages from 0.1 mg/day per 50 kg body weight to 25 μg/day, and even more preferably oral administration of tyrosine and iodine in dosages of 10 mg to 10 g/day per 50 kg body weight.

$T_3$ and more potently, $T_4$ affects cell division and angiogenesis through binding to integrin $\alpha V\beta 3$, commonly overexpressed on many cancer cells [18]. Acting via a cell surface receptor, thyroid hormone is a growth factor for glioma cells [19].

BRIEF DESCRIPTION OF THE DRAWINGS

In order to understand the invention and to see how it may be carried out in practice, embodiments will now be described, by way of non-limiting example only, with reference to the accompanying drawings, in which:

(FIG. 1A-1D) Diagnosis (FIG. 1E-1H) At progression, after 9 months of temozolomide (an oral alkylating agent) treatment, note new FLAIR signal along the left optic radiations (arrow) (FIG. 1I-1L) Improvement 4 weeks after combined Propylthiouracil (PTU)+carboplatinum treatment (FIG. 1M-1P) Near resolution of FLAIR hyper intense changes 18 months later.

FIGS. 3A-3E are brain MRI scans of T-1-weighted with gadolinium on disease recurrence, where FIG. 3A shows disease recurrence measured on May 2009. FIG. 3B shows tumor status 3 month thereafter. FIG. 3C shows tumor status 4 month thereafter, showing no response to treatment and tumor progression. FIG. 3D shows tumor status one month thereafter, showing response to combined bevacizumab+carboplatin+PTU+Cytomel® treatment. FIG. 3E shows the continuous response 4 months thereafter using the same treatment. Tumor is marked in all figures by a white arrow.

SUMMARY OF THE INVENTION

Figure 1D:
Figure 1H:
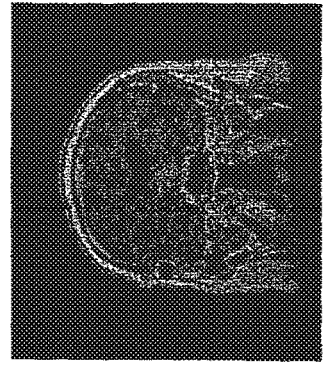
Figure 1C:
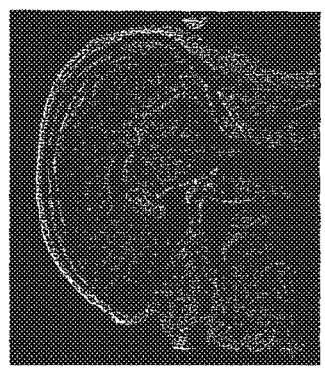
Figure 1G:
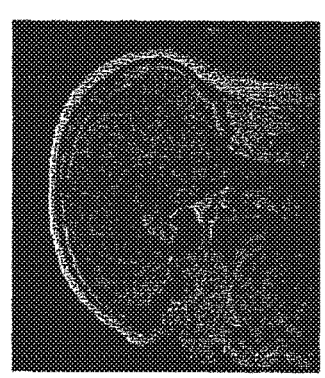
Figure 1B:
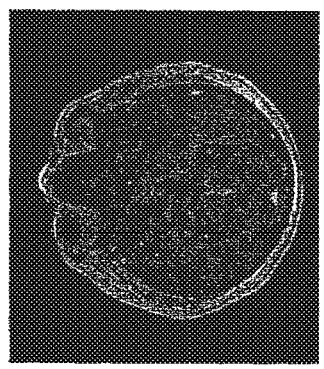
Figure 1F:
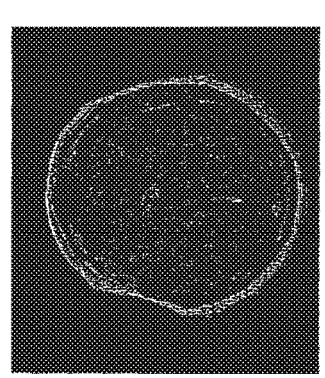
Figure 1A:
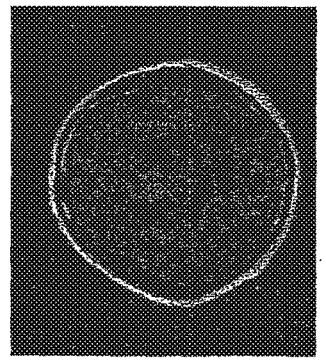
FIGS. 1A-1P are brain MRI scans showing response to carboplatinum treatment. Row 1 depicts T-1 weighted fluid-attenuated invasion recovery (FLAIR). Rows 2-4, T1-weighted with gadolinium, shown at horizontal (rows 1 and 2), sagittal (row 3) and coronal views (row 4).
Figure 1E:
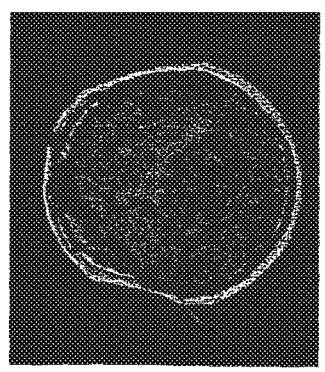
Figure 1L:
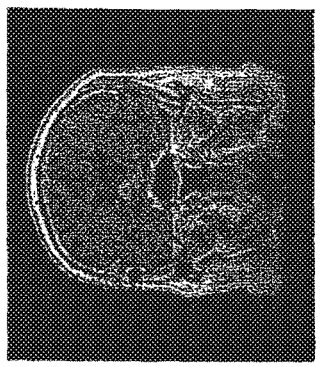
Figure 1P:
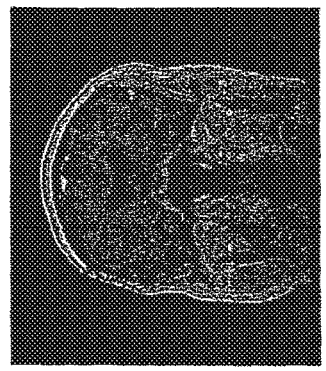
Figure 1K:
Figure 1O:
Figure 1J:
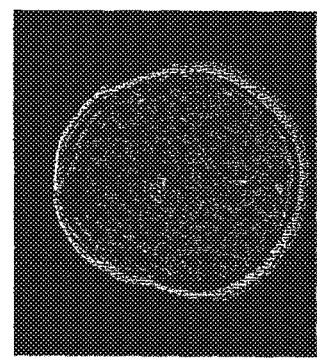
Figure 1N:
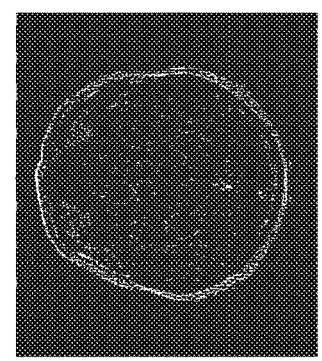
Figure 1I:
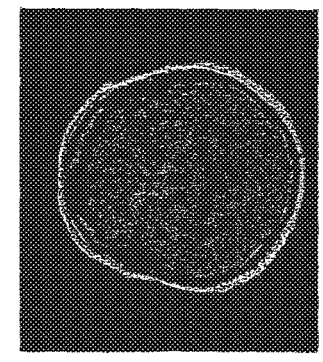
Figure 1M:
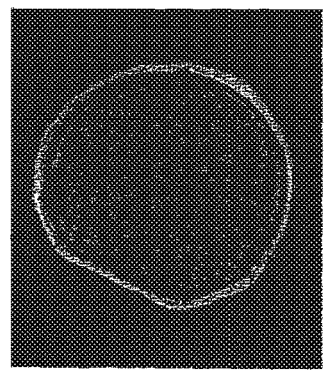

In a first aspect the present invention provides a therapeutic method comprising administering to a subject in need of a therapeutic treatment:
  (i) a triiodothyronine ($T_3$) or biochemical analogue thereof; and
  (ii) at least one anti-thyroid treatment selected from the group consisting of treatment with an anti-thyroid agent, treatment with radioiodine and surgical removal of all or part of the thyroid gland.

In a second aspect the present invention provides the use of triiodothyronine ($T_3$) or biochemical analogue thereof for treating a subject undergoing at least one anti-thyroid treatment selected from the group consisting of treatment with an anti-thyroid agent, treatment with radioiodine and surgical removal of all or part of the thyroid gland.

In a third aspect the present invention provides the use of triiodothyronine ($T_3$) or biochemical analogue thereof for the preparation of a pharmaceutical composition for treating a subject being treated with at least one anti-thyroid treatment selected from the group consisting of treatment with an anti-thyroid agent, treatment with radioiodine and surgical removal of all or part of the thyroid gland.

In a fourth aspect the present invention provides a kit comprising:
  a first package of a dosage form of $T_3$ or a biochemical analogue thereof,
  a second package of a dosage form of at least one anti-thyroid agent, and
  instructions for combined therapy of a subject using the first dosage forms and the second dosage forms.

In a fifth aspect the present invention provides a pharmaceutical composition comprising:
  (i) triiodothyronine ($T_3$) or biochemical analogue thereof, and
  (ii) at least one anti-thyroid agent.

DETAILED DESCRIPTION OF SOME NON-LIMITING EMBODIMENTS

The present invention is based on the following empirical findings:
  treatment of cancer patients with Cytomel®, a synthetic $T_3$ thyroid hormone (at 5-40 μg/day) resulted in decrease in $T_4$ levels and thus slows the growth of the cancer. These clinical findings correlated with the subject being at a state of moderate hypothyroidism, as indicated by the low levels (below normal) of $T_4$ in the subject's blood and above normal values of TSH;
  combined treatment of cancer subjects with an anti-thyroid agent, such as methimazole or PTU, in combination with Cytomel®, slowed tumor growth and/or enhanced sensitivity of the tumor cells to chemotherapy and/or radiation therapy.

Thus, in accordance with a first of its aspects, there is provided a therapeutic method comprising administering to a subject in need of a therapeutic treatment with:
  (i) triiodothyronine ($T_3$) or biochemical analogue thereof; and
  (ii) at least one anti-thyroid treatment selected from the group consisting of treatment with an anti-thyroid agent, treatment with radioiodine and surgical removal of all or part of the thyroid gland.

As used herein, the term "biochemical analogue" of $T_3$ denotes any compound having a thyronine backbone and exhibits at least partial $T_3$ hormonal activity. In some embodiments, the $T_3$ biochemical analogue is an L-isomer of $T_3$. In some other embodiments, the $T_3$ biochemical analogue is an iodine derivative of thyronine. In yet some other embodiments, the $T_3$ biochemical analogue is an L-isomer of $T_3$ is liothyronine sodium.

Preferably, the biochemical analogue is an iodine derivative of thyronine. Such iodinated derivatives may be prepared by methods known in the art, such as that described by Gunther Hillman in Great Britain patent No. GB 851,610 titled: Methods of producing iodine derivatives of thyronine. A non-limiting list of iodine derivatives of thyronine include 3',5',3-triiodothyronine ($rT_3$), $rT_3$ derived hormone, such as 3',3-diiodothyronine, 3',5'-diiodothyronine, 5',3-diiodothyronine, 3'-iodothyronine, 5'-iodothyronine, 3-iodothyronine, 3'-bromo-5'-iodo-3,5-di-iodothyronine, 3'-chloro-5'-iodo-3,5-di-iodothyronine, isomer of 3,5,3'-triiodothyronine, e.g. triiodothyropropionic acid as well as the L-isomer of tri-iodothyronine. In one particular embodiment of the invention, the biochemical analogue is Liothyronine sodium being the L-isomer of triiodothyronine ($LT_3$), (marketed under the brand name Cytomel® or Tertroxin® in Australia).

Other biochemical analogues may include amides of iodothyronine compounds, such as those described by Cree Gavin et al. in U.S. Pat. No. 4,426,453 titled: Derivatives of iodothyronine compounds and their use in an assay for the free iodothyronine compounds.

The biochemical analogue of $T_3$ exhibit at least partially $T_3$ hormonal activity sufficient to, for example, signal the hypophysis that there is enough $T_3$ in the circulation and resulting in reduction of $T_4$ production.

The term "anti-thyroid treatment" is used to denote treatment with an anti-thyroid agent, treatment with radioiodine ($I^{131}$) to destroy the thyroid gland or thyroidectomy treatment to remove part or all of the thyroid gland (thyroidectomy treatment may consist of hemithyroidectomy (or "unilateral lobectomy") in which only half of the thyroid is removed or isthmectomy in which the band of tissue (or isthmus) connecting the two lobes of the thyroid is removed).

The anti-thyroid agent, as defined herein, is any chemical or biological agent that is capable of decreasing the amount of thyroid hormone produced by the thyroid gland. There are a variety of anti-thyroid agents known in the art.

In some embodiments, the anti-thyroid agent is a thioamide based drug.

Without being limited thereto, the anti-thyroid agent is selected from propylthiouracil (PTU), methimazole (also known as Tapazole® or Thiamazole®) and Carbimazole.

In some embodiments, e.g. when referring to treatment of a subject having cancer, the method of the invention comprises administration of Methimazole in an amount between 10 mg and 80 mg per day, or of PTU in an amount of between 100 mg and 1200 mg per day.

Generally, in the context of the present invention, the term "treatment", "treating" or any lingual variation thereof, is used herein to refer to obtaining a desired pharmacological and physiological effect on the subject's well being. As such, the effect may be prophylactic in terms of preventing or partially preventing an undesired condition or undesired symptoms in the subject in predisposition of developing the condition and/or may be therapeutic in terms of curing or partially curing of an already existing undesired condition, symptom or adverse effect attributed to the condition. Thus, the term "treatment", as used herein, covers any of the following (a) preventing the condition from occurring in a subject which may be predisposed to have the condition (e.g. cancer) but has not yet been diagnosed as having it, e.g. the clinical symptoms of the condition have not yet being developed to a detectable level; (b) inhibiting the condition from developing or its clinical symptoms, such as fever or inflammation; or (c) causing regression of the condition and/or its symptoms.

In one embodiment, the method of the present invention is effective to treat a subject having cancer. In accordance with this embodiment, the treatment may be effective to achieve at least one of the following:

(a) sensitization in the subject of cancer to anti-cancer treatment;
(b) treating cancer cells.

In the context of the cancer treatment, the term "sensitization to anti cancer treatment" is used to denote an effect of treatment with the at least one anti-thyroid treatment and $T_3$ or biochemical analogue thereof that results in a statistically significant sensitivity of the cancer cells to anti-cancer treatment Thus, sensitization may include increase in sensitivity of the cancer cells to the anti-cancer treatment as well as causing drug resistant cells to become sensitive to the anti-cancer treatment (e.g. in case of multi-drug resistant cells). In some embodiments, sensitization may thus permit reduction in a required amount of anti cancer treatment (such as chemotherapeutic drug or radiotherapy) that would be otherwise required without sensitization.

The anti-cancer treatment in accordance with some embodiments of the invention may be one or more selected from the group consisting of chemotherapy, radiotherapy monoclonal antibody therapy, angiogenesis inhibitor therapy, biological therapy, bone marrow transplantation, peripheral blood stem cell transplantation, gene therapy for cancer, hyperthermia, laser therapy, photodynamic therapy, and targeted cancer therapies.

In some embodiments chemotherapy comprises treatment with one or more chemotherapeutic drug selected from alkylating agents, antimetabolites, anthracyclines, plant alkaloids, topoisomerase inhibitors, or any other antitumor agents which affect cell division or DNA synthesis and function in some way. Some none limiting examples of chemotherapeutic drugs which are used in the context of the present invention include Amsacrine (Amsidine®); Bleomycin, Busulfan, Capecitabine (Xeloda®), Carboplatin, Carmustine (BCNU®), Chlorambucil (Leukeran®), Cisplatin, Cladribine (Leustat®), Clofarabine (Evoltra), Crisantaspase (Erwinase®), Cyclophosphamide, Cytarabine (ARA-C), Dacarbazine (DTIC®), Dactinomycin (Actinomycin D®), Daunorubicin Docetaxel (Taxotere®), Doxorubicin, Epirubicin, Etoposide (Vepesid®, VP-16®), Fludarabine (Fludara®), Fluorouracil (5-FU®), Gemcitabine (Gemzar®), Hydroxyurea (Hydroxycarbamide, Hydre®a), Idarubicin (Zavedos), Ifosfamide (Mitoxana), Irinotecan (CPT-11®, Campto®), Leucovorin (folinic acid), Liposomal doxorubicin (Caelyx®, Myocet®), Liposomal daunorubicin (DaunoXome®) Lomustine, Melphalan, Mercaptopurine, Mesna, Methotrexate, Mitomycin Mitoxantrone, Oxaliplatin (Eloxatin®), Paclitaxel (Taxol®), Pemetrexed (Alimta®) Pentostatin (Nipent®), Procarbazine, Raltitrexed (Tomudex®), Streptozocin (Zanosar®), Tegafur-uracil (Uftoral®), Temozolomide (Temodal®) Teniposide (Vumon®).

The method of the invention may also be effective to treat cancer cells. Treatment of cancer cells, in the context of the invention, is to be understood as any effect on the cells that results in one or more of reducing the volume of the cancer cells, inhibiting or causing cession of proliferation of the cancer cells, causing cancer cell death (e.g. apoptosis, necrosis etc), eliminating the cells from the subject's body, inducing cell cycle arrest.

As used herein, "cancer" which is used interchangeably with the term "cancer cells" refers to any type of cells that are associated with the formation of a cancerous tumor. In some embodiments the cancer is selected from the group consisting of carcinoma, sarcoma, lymphoma and leukemia, germ cell tumor and blastoma.

In some embodiments, the cancer cells treated by the method of the invention are those associated with solid tumors or liquid tumors.

Non-limiting examples of solid tumors include wherein the solid cancer is selected from the group consisting of vascularized tumors, gonadal cancers, gastrointestinal, esophageal cancer, Barrett's esophagus cancer, oral cancer, parotid cancer, nasopharyngeal cancer, thyroid cancer, CNS cancers, urogenital cancers, skin cancers bone and connective tissue cancers. In one embodiment, the solid cancer is glioma, e.g. glioblastoma.

Non-limiting examples of liquid tumors include multiple myeloma, Waldenstroms' (IgM) gammopathy, Bergers (IgA), CNS lymphoma (e.g., associated with AIDS), gonadal lymphomas and leukemias, mantle cell lymphomas, vascularized stages of leukemias (bone marrow) and lymphomas (in the lymph nodes), and any other leukemia or lymphoma, including low grade leukemias and lymphomas.

In yet some embodiments, the cancer cells are malignant cancer cells.

In accordance with the method of the invention, the subject may be administered with $T_3$ or the analogue thereof simultaneously, concomitantly or separately, e.g. within a time interval from the anti-thyroid treatment. In some embodiments especially when aimed at treating cancer, the method of the invention comprises continuous treatment of the subject for a period of at least 4 weeks.

The method of the present invention may be performed in conjunction with other treatments. In one embodiment, where the method of the invention is applicable for treating cancer, it may be performed in conjugation with one other anti-cancer therapy (e.g. chemotherapy, radiotherapy, hyperthermia, biologic therapy). In some embodiment the method of the invention is performed in conjunction with another therapy which is not directly aimed at the treating of cancer (e.g., surgery, hormone replacement therapy).

The invention also provides the use of $T_3$ or biochemical analogue thereof for treating a subject undergoing at least one anti-thyroid treatment selected from the group consisting of treatment with an anti-thyroid agent, treatment with radioiodine and surgical removal of all or part of the thyroid gland.

Further, the invention provides the use of $T_3$ or biochemical analogue thereof for the preparation of a pharmaceutical composition for treating a subject being treated with at least one anti-thyroid treatment selected from the group consisting of treatment with an anti-thyroid agent, treatment with radioiodine and surgical removal of all or part of the thyroid gland.

The use of the invention is, in accordance with some embodiments, for treating a subject having cancer or for the preparation of a pharmaceutical composition for treating cancer, the treatment and cancer being as defined hereinabove.

Further, the invention provides a kit comprising:
  a first package of a dosage form of $T_3$ or a biochemical analogue thereof,
  a second package of a dosage form of at least one anti-thyroid agent, and
  instructions for combined therapy of a subject using the first dosage forms and the second dosage forms.

In some embodiments, the instructions comprise administering the $T_3$ or a biochemical analogue thereof and the at least one anti-thyroid agent to a subject having cancer.

The kit of the invention is applicable, in accordance with some embodiments of the invention, to provide the dosage form of $T_3$ or a biochemical analogue thereof and the dosage form of the at least one anti-thyroid agent; in an amount are sufficient to achieve one or more effect selected from:
  (a) sensitization of the cancer to anti-cancer treatment;
  (b) treating the cancer.

The $T_3$ or analogue thereof and the anti-thyroid agent may be provided to the subject in need thereof separately, or in a single composition.

Thus, the invention also provides a pharmaceutical composition comprising:
  (i) triiodothyronine ($T_3$) or biochemical analogue thereof, and
  (ii) at least one anti-thyroid agent.

In one embodiment, the composition is for treating cancer, the cancer being as defined hereinabove.

In yet some other embodiments, the composition is effective to achieve one or more of:
  (a) sensitization of the cancer to anti-cancer treatment, as defined hereinabove;
  (b) treating the cancer, as defined hereinabove.

The $T_3$ or analogue thereof and the anti-thyroid agent may be provided to the subject in various forms, including gastrointestinal administration (e.g. oral in tablets, capsules, drops, syrup or suspension); rectal; by mean of gavage; sublingual; sublabial; administration through the central nervous system (e.g. epidural, intracerebral, intracerebroventricular), administration via other locations such as epicutaneous, intradermal, subcutaneous, nasal, intravenous, intraarterial, intramuscular, intracardiac, intraosseous infusion, intrathecal, intraperitoneal, intravesical, intravitreal, intracavernous injection, intravaginal and intrauterine.

In one embodiment, the $T_3$ or analogue thereof and the anti-thyroid agent are provided together or separately in one or more formulations suitable for oral administration, such as, without being limited thereto, pills, tablets, capsules, suspension, syrups, drops etc.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

As used herein, the singular form "a", "an" and "the" include plural references unless the context clearly dictates otherwise. For example, the term "an anti-thyroid agent" may independently include a plurality of agents, including a variety thereof.

Further, as used herein, the term "comprising" is intended to mean one or more of the recited elements. The term "consisting essentially of" is used to define the recited elements while excluding other elements. "Consisting of" shall thus mean excluding more than trace amounts of elements that are not recited. Embodiments defined by each of these transition terms are within the scope of this invention.

Further, all numerical values, e.g. when referring the amounts or ranges of the elements constituting the invention are approximations which are varied (+) or (−) by up to 20%, at times by up to 10% of from the stated values. It is to be understood, even if not always explicitly stated that all numerical designations are preceded by the term "about".

Various embodiments and aspects of the present invention as delineated hereinabove and as claimed in the claims section below find experimental support in the following examples which are not in any way intended to limit the scope of the inventions as claimed.

LIST OF EMBODIMENTS

Disclosed below are some non-limiting embodiments of the invention, provided in the form of numbered paragraphs.
1. A therapeutic method comprising administering to a subject in need of a therapeutic treatment:
  (i) a triiodothyronine ($T_3$) or biochemical analogue thereof; and
  (ii) at least one anti-thyroid treatment selected from the group consisting of treatment with an anti-thyroid agent, treatment with radioiodine and surgical removal of all or part of the thyroid gland.
2. The therapeutic method of Embodiment 1, comprising treating a subject having cancer.
3. The therapeutic method of Embodiment 2, wherein the treatment is effective to achieve at least one of the following:
  (a) sensitization in the subject of cancer to anti-cancer treatment;
  (b) treating the cancer.

4. The therapeutic method of any one of Embodiments 1 to 3, wherein said biochemical analogue of $T_3$ exhibit at least partial hormonal activity of said $T_3$.

5. The therapeutic method of Embodiment 4, wherein said biochemical analogue is an L-isomer of $T_3$.

6. The therapeutic method of Embodiment 5, wherein said L-isomer of $T_3$ is liothyronine sodium.

7. The therapeutic method of any one of Embodiments 1 to 6, comprising treatment of the subject with a daily amount of $T_3$ or biochemical analogue thereof.

8. The therapeutic method of Embodiment 7, wherein the daily amount of $T_3$ or biochemical analogue thereof exhibits at least part of the activity of liothyronine sodium.

9. The therapeutic method of Embodiment 7 or 8, wherein the daily amount of $T_3$ or biochemical analogue thereof is between about 5 μg and between about 40 μg.

10. The therapeutic method of any one of Embodiments 7 to 9, comprising administration of the $T_3$ or biochemical analogue thereof once a day or several times a day.

11. The therapeutic method of any one of Embodiments 1 to 10, wherein the $T_3$ or biochemical analogue thereof is administered orally, intravenously or intramuscularly to the subject.

12. The therapeutic method of any one of Embodiments 2 to 11, wherein the cancer is solid cancer.

13. The therapeutic method of Embodiment 12, wherein the solid cancer is selected from the group consisting of vascularized tumors, gonadal cancers, gastrointestinal, esophageal cancer, Barrett's esophagus cancer, oral cancer, parotid cancer, nasopharyngeal cancer, thyroid cancer, CNS cancers, urogenital cancers, skin cancers bone and connective tissue cancers.

14. The therapeutic method of Embodiment 13, wherein the solid cancer is glioma.

15. The therapeutic method of Embodiment 14, wherein the glioma is glioblastoma.

16. The therapeutic method of any one of Embodiments 1 to 15 wherein the anti-thyroid agent is a thioamide based drug.

17. The therapeutic method of Embodiment 16, wherein the thioamide based drug is propylthiouracil (PTU) or methimazole.

18. The therapeutic method of Embodiment 16, comprising administration of Methimazole in an amount between 10 mg and 80 mg per day, or of PTU in an amount of between 100 mg and 1200 mg per day.

19. The therapeutic method of any one of Embodiments 1 to 18, in combination with at least one anti-cancer treatment.

20. The therapeutic method of Embodiment 19, wherein the anti-cancer treatment is selected from the group consisting of chemotherapy, radiotherapy, monoclonal antibody therapy, angiogenesis inhibitor therapy, biological therapy, bone marrow transplantation, peripheral blood stem cell transplantation, gene therapy, hyperthermia, laser therapy, photodynamic therapy, targeted cancer therapies.

21. The therapeutic method of any one of Embodiments 1 to 20, wherein the $T_3$ or biochemical analogue thereof and the anti-thyroid agent are administered to the subject concomitantly or separately.

22. The therapeutic method of any one of Embodiments 1 to 21, comprising continuous treatment of the subject for a period of at least 4 weeks.

23. Triiodothyronine ($T_3$) or biochemical analogue thereof for use in treating a subject undergoing at least one anti-thyroid treatment selected from the group consisting of treatment with an anti-thyroid agent, treatment with radioiodine and surgical removal of all or part of the thyroid gland.

24. Use of triiodothyronine ($T_3$) or biochemical analogue thereof for the preparation of a pharmaceutical composition for treating a subject being treated with at least one anti-thyroid treatment selected from the group consisting of treatment with an anti-thyroid agent, treatment with radioiodine and surgical removal of all or part of the thyroid gland.

25. Triiodothyronine ($T_3$) or biochemical analogue thereof for use in combination with at least one anti-thyroid agent, in the preparation of a pharmaceutical composition.

26. The $T_3$ or biochemical analogue thereof of Embodiments 23 or 25, for use in treating a subject having cancer.

27. The $T_3$ or biochemical analogue thereof of Embodiments 23 or 25-26, wherein treatment with the $T_3$ or biochemical analogue thereof with the at least one anti-thyroid treatment is in an amount effective to achieve one or more of:
   (a) sensitization of the cancer to anti-cancer treatment;
   (b) treating the cancer.

28. The $T_3$ or biochemical analogue thereof of any one of Embodiments 23 or 25-27, wherein said biochemical analogue of $T_3$ exhibits at least partial hormonal activity of said $T_3$.

29. The $T_3$ or biochemical analogue thereof of Embodiment 28, wherein said biochemical analogue is an L-isomer of $T_3$.

30. The $T_3$ or biochemical analogue thereof of Embodiment 29, wherein said L-isomer of $T_3$ is liothyronine sodium.

31. The $T_3$ or biochemical analogue thereof of Embodiment 30, wherein the amount of the L-isomer of $T_3$ is liothyronine sodium is adapted for daily administration of between about 5 μg and between about 40 μg.

32. The $T_3$ or biochemical analogue thereof of any one of Embodiments 23 or 25-31, wherein the $T_3$ or biochemical analogue thereof is adapted for administration to the subject orally, intravenously or intramuscularly.

33. The $T_3$ or biochemical analogue thereof of any one of Embodiments 25 to 32, wherein the cancer is solid cancer.

34. The $T_3$ or biochemical analogue thereof of Embodiment 33, wherein the solid cancer is selected from the group consisting of vascularized tumors, gonadal cancers, gastrointestinal, esophageal cancer, Barrett's esophagus cancer, oral cancer, parotid cancer, nasopharyngeal cancer, thyroid cancer, CNS cancers, urogenital cancers, skin cancers bone and connective tissue cancers.

35. The $T_3$ or biochemical analogue thereof of Embodiment 34, wherein the solid cancer is glioma.

36. The $T_3$ or biochemical analogue thereof of Embodiment 35, wherein the glioma is glioblastoma.

37. The $T_3$ or biochemical analogue thereof of any one of Embodiments 23 or 25-36 wherein the anti-thyroid agent is a thioamide based drug.

38. The $T_3$ or biochemical analogue thereof of Embodiment 37, wherein the thioamide based drug is propylthiouracil (PTU) or methimazole.

39. A kit comprising:
   a first package of a dosage form of $T_3$ or a biochemical analogue thereof,
   a second package of a dosage form of at least one anti-thyroid agent, and
   instructions for combined therapy of a subject using the first dosage forms and the second dosage forms.

40. The kit of Embodiment 39, wherein the instructions comprise administering the $T_3$ or a biochemical analogue thereof and the at least one anti-thyroid agent to a subject having cancer.

41. The kit of Embodiment 40, wherein the dosage form of $T_3$ or a biochemical analogue thereof and the dosage form of the at least one anti-thyroid agent; are sufficient to achieve one or more effect selected from:

(a) sensitization of the cancer to anti-cancer treatment;
(b) treating the cancer.

42. The kit of any one of Embodiments 39 to 41, wherein the biochemical analogue of $T_3$ exhibit at least partial hormonal activity of said $T_3$.

43. The kit of Embodiment 42, wherein the biochemical analogue is an L-isomer of $T_3$.

44. The kit of Embodiment 43, wherein said L-isomer of $T_3$ is liothyronine sodium.

45. The kit of any one of Embodiments 39 to 44, wherein the instructions comprise daily administration of the dosage form of $T_3$ or biochemical analogue thereof.

46. The kit of Embodiment 45, wherein the dosage form of $T_3$ or biochemical analogue thereof exhibits at least part of the activity of liothyronine sodium.

47. The kit of Embodiment 45 or 46, wherein the dosage form of $T_3$ or biochemical analogue thereof comprises between about 5 μg and between about 40 μg.

48. The kit of any one of Embodiments 45 to 47, wherein the instructions comprise administration of $T_3$ or biochemical analogue thereof once a day or several times a day.

49. The kit of any one of Embodiments 45 to 48 wherein the instructions comprise administration of $T_3$ or biochemical analogue thereof orally, intravenously or intramuscularly.

50. The kit of any one of Embodiments 45 to 49, wherein the cancer is solid cancer.

51. The kit of Embodiment 50, wherein the solid cancer is selected from the group consisting of vascularized tumors, gonadal cancers, gastrointestinal, esophageal cancer, Barrett's esophagus cancer, oral cancer, parotid cancer, nasopharyngeal cancer, thyroid cancer, CNS cancers, urogenital cancers, skin cancers bone and connective tissue cancers.

52. The kit of Embodiment 51 wherein the solid cancer is glioma.

53. The kit of Embodiment 52, wherein the glioma is glioblastoma.

54. The kit of any one of Embodiments 45 to 53 wherein the anti-thyroid agent is a thioamide based drug.

55. The kit of Embodiment 54, wherein the thioamide based drug is propylthiouracil (PTU) or methimazole.

56. The kit of Embodiment 55, wherein a dosage form of Methimazole comprises an amount of between 10 mg and 80 mg a dosage form of PTU is in an amount of between 100 mg and 1200 mg.

57. The kit of any one of Embodiments 45 to 56, wherein the instructions comprise treating the subject with at least one anti-cancer treatment.

58. The kit of Embodiment 57, wherein the anti-cancer treatment is selected from the group consisting of chemotherapy, radiotherapy, monoclonal antibody therapy, angiogenesis inhibitor therapy, biological therapy, bone marrow transplantation, peripheral blood stem cell transplantation, gene therapy, hyperthermia, laser therapy, photodynamic therapy, targeted cancer therapies.

59. The kit of any one of Embodiments 45 to 58, wherein the instructions comprise concomitant or separate administration of the first dosage form and the second dosage form.

60. The kit of any one of Embodiments 45 to 59, wherein the instructions comprise continuous treatment of the subject for a period of at least 4 weeks.

61. A pharmaceutical composition comprising:
   (i) triiodothyronine ($T_3$) or biochemical analogue thereof, and
   (ii) at least one anti-thyroid agent.

62. The pharmaceutical composition of Embodiment 61, for treating cancer.

63. The pharmaceutical composition of Embodiment 62, being effective to achieve at least one of the following:
   (a) sensitization of the cancer to anti-cancer treatment;
   (b) treating the cancer.

64. The pharmaceutical composition of any one of Embodiments 61 to 63, wherein the biochemical analogue of $T_3$ exhibit at least partial hormonal activity of said $T_3$.

65. The pharmaceutical composition of Embodiment 64, wherein the biochemical analogue is an L-isomer of $T_3$.

66. The pharmaceutical composition of Embodiment 65, wherein the L-isomer of $T_3$ is liothyronine sodium.

67. The pharmaceutical composition of any one of Embodiments 61 to 66, comprising an amount of $T_3$ or biochemical analogue thereof adapted for daily administration.

68. The pharmaceutical composition of Embodiment 67, wherein the amount of $T_3$ or biochemical analogue thereof for daily administration is between about 5 μg and between about 40 μg.

69. The pharmaceutical composition of any one of Embodiments 61 to 68, formulated for oral, intravenous or intramuscular administration.

70. The pharmaceutical composition of any one of Embodiments 64 to 69, for treating a solid cancer.

71. The pharmaceutical composition of Embodiment 70, wherein the solid cancer is selected from the group consisting of vascularized tumors, gonadal cancers, gastrointestinal, esophageal cancer, Barrett's esophagus cancer, oral cancer, parotid cancer, nasopharyngeal cancer, thyroid cancer, CNS cancers, urogenital cancers, skin cancers bone and connective tissue cancers.

72. The pharmaceutical composition of Embodiment 71, wherein the solid cancer is glioma.

73. The pharmaceutical composition of Embodiment 72, wherein the glioma is glioblastoma.

74. The pharmaceutical composition of any one of Embodiments 61 to 73 wherein the anti-thyroid agent is a thioamide based drug.

75. The pharmaceutical composition of Embodiment 74, wherein the thioamide based drug is propylthiouracil (PTU) or methimazole.

76. The pharmaceutical composition of Embodiment 75, comprising Methimazole in an amount for daily administration of between 10 mg and 80 mg, or PTU in an amount for daily administration of between 100 mg and 1200 mg.

DESCRIPTION OF NON-LIMITING EXAMPLES

Examples of hypothyroidism induced by anti thyroid drugs such as PTU or Metimazole combined with $T_3$ (Cytomel®): These examples will show that anti-thyroid treatment such as PTU/methimazole in combination with $T_3$ or analogue thereof, induce a quick (2-4 weeks) decrease in $FT_4$ levels.

Example 1

A 64 year old Caucasian male subject, presented with right eye visual loss that developed over several weeks. Magnetic Resonance Imaging (MRI) revealed a space occupying lesion in the sellar and suprasellar regions of the brain (FIGS. 1A-1D). The process involved the right optic tract and extended intracranially to the optic chiasm along the right optic nerve and to the hypothalamus and the third ventricle near the Foramen of Monro. Open biopsy was performed a week after MRI. The pathological diagnosis revealed characteristic grade IV glioblastoma (GBM) histological appearance.

Following the above findings, the subject was initially treated with the standard protocol for newly diagnosed GBM, which included focal radiation with concurrent oral administration of temozolomide, followed by 9 cycles of monthly 5-day regimen of temozolomide treatment. During that time a further decline in vision was observed as well as an increased tumor size observed on MRI (FIGS. 1E-1H).

Figure 2:
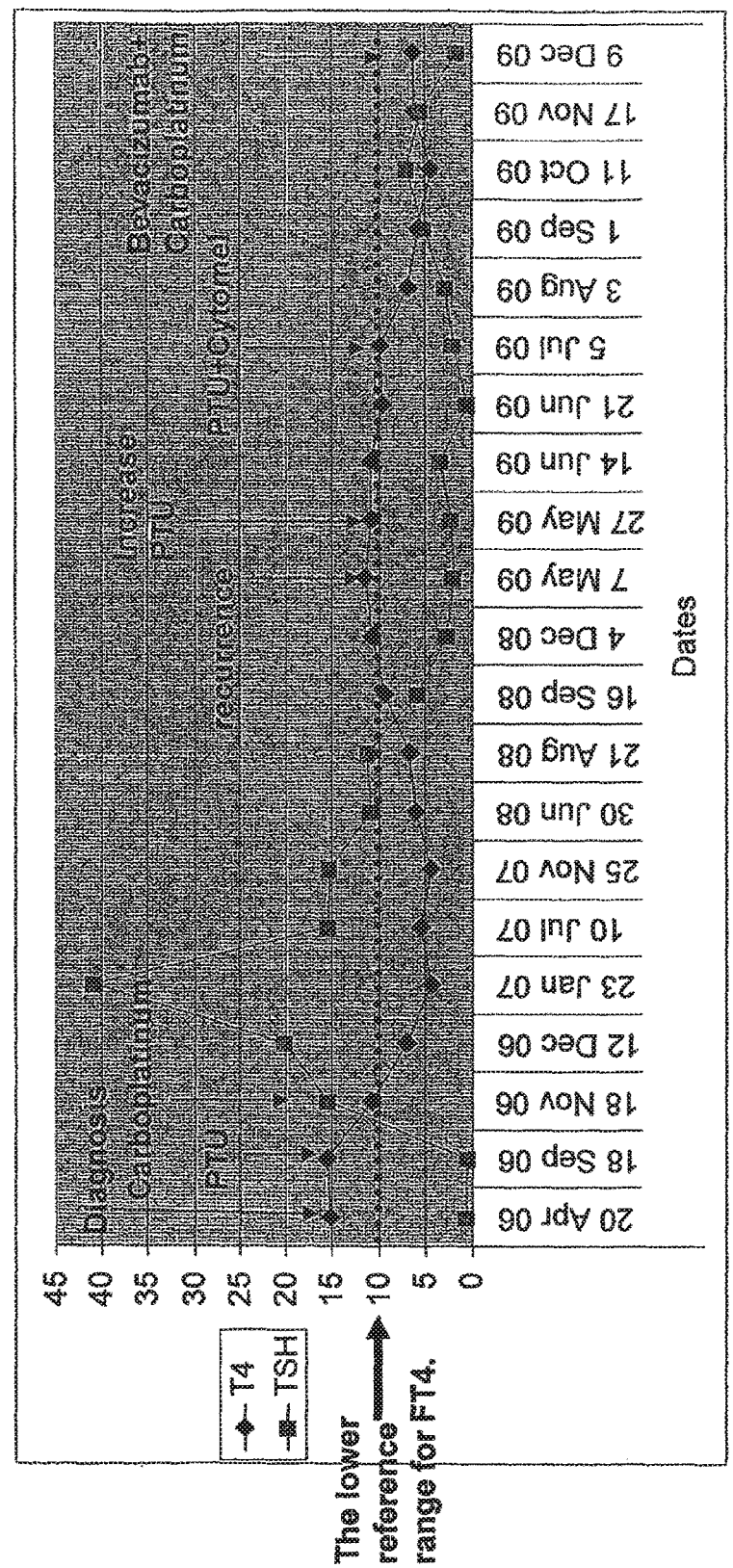
FIG. 2 is a graph showing free $T_4$ and TSH levels under hypothyroid induction therapy from disease diagnosis of patient in Example 1 till start of bevacizumab+carboplatinum. Y axis indicates the level of either free $T_4$ (pmol/l, ◆) or TSH (micIU/ml, ■). X axis indicates the dates of the individual blood tests. Vertical arrows denote specific dates of disease analysis and various treatments for hypothyroid induction (PTU alone and combined with liothyronine sodium (Cytomel®)) and selected chemotherapy treatments.
Figure 4A:
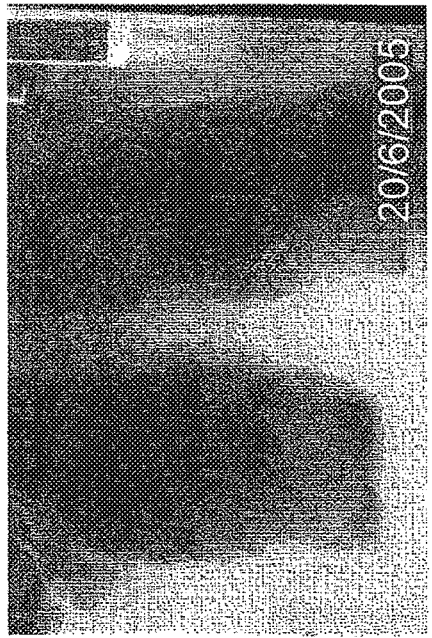
Figure 4B:
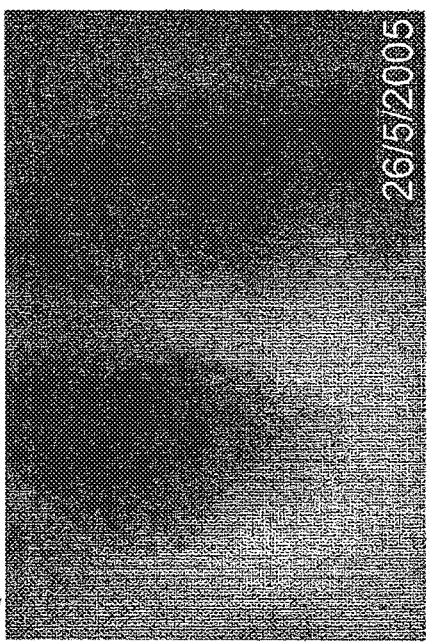
Figure 4C:
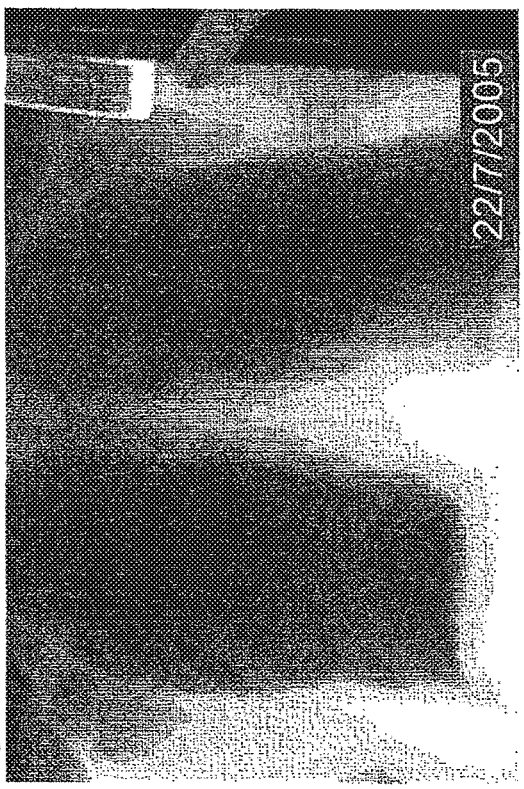

After 6 months on temozolomide treatment, the subject started treatment, in parallel, with a thyroid function inhibiting drug, propylthiouracil (PTU), at 600 mg/day and was monitored weekly for TSH and free $T_4$ levels (FIG. 2). The subject's $T_4$ levels slightly reduced after about 12 weeks of treatment. Shortly thereafter carboplatin treatment (7 mg/kg) was initiated along with continuation of the thyroid reduction therapy, using 600 mg/day PTU. Four weeks after beginning carboplatin+PTU treatment, reduced enhancement of the tumor extending into the left optic tract was observed (FIGS. 1I-1L, marked by an arrow). Complete response of the tumor to the combined treatment was sustained through 15 cycles of treatment (FIG. 1M-1P). After 15 cycles, as the carbolatin treatment was stopped and the patient was maintained on PTU (200-400 mg) alone for additional 12 month.

About two years later, concomitant with an increase in the subject's $FT_4$ level (FIG. 2), MRI demonstrated tumor recurrence that continued to progressively enlarge (FIGS. 3A-3C). The subject then received two courses of carboplatin, while still not hypothroxinemic, with no response. In order to achieve hypothyroxinemia, in addition to PTU, 5 μg of triiodotionine ($T_3$) was added 3 times a day in order to inhibit TSH and reduce thyroxine level. Within 3 weeks the subject became hypothyroxinemic (FIG. 2). Following several lines of treatment (several months), with no response (FIGS. 3B-3C), the subject started treatment with Bevacizumab (600 mg) every 3 weeks, combined with Carboplatin (500 mg) every 6 weeks. Within 4 weeks, major ongoing response was observed by MRI (FIGS. 3D-3E).

Example 2

A female subject was presented with a malignant fibrous histiocytoma (MFH) of the left pulmonary vein. The tumor filled the left chest cavity and invaded the left atrium. The tumor was resected but recurred within 4 months.

A course of palliative radiation therapy (46Gy) was initiated along with methimazole (40 mg/day) treatment. However, after 2 months of treatment, no change in free $T_4$ level or tumor size was observed. At that time point, the subject received combined treatment including methimazole and Cytomel® (5 μg×3/day) and after 3-4 weeks of treatment with methimazole and Cytomel® the subject became hypothyroxineemic (low free $T_4$, below reference range). Second line chemotherapy was given, including Carobopla-tin and Taxol® (a plant alkaloid chemotherapy drug) every three weeks in combination with methimazole/Cytomel® treatment, which resulted with a reduction of more than 80% in the tumor mass. The subject then underwent resection of the mass which was found to be mostly necrotic. The subject was maintained on Cytomel® 5 μg, three times a day and methimazole (reduced to 30 mg once a day). As a result of this combined treatment, the subject exhibited excellent post operative performance status and returned to work.

The invention claimed is:

1. A therapeutic method for treating a cancer patient who is being concomitantly treated with an anti-cancer therapy, comprising treating the patient with a therapeutic combination comprising:
   (i) a triiodothyronine ($T_3$) or biochemical analogue thereof that exhibits at least partial $T_3$ hormonal activity, said biochemical analogue being an iodine derivative of thyronine, or an L-isomer of $T_3$; and
   (ii) at least one anti-thyroid agent,
   wherein said $T_3$ or biochemical analogue thereof is administered to said subject daily, at a daily amount of between about 5 μg and about 40 μg for a period of at least 3 weeks;
   wherein said anti-thyroid agent is administered in an amount that decreases the amount of thyroid hormone produced by the thyroid gland; and
   wherein said T3 or biochemical analogue thereof is concomitantly administered with said at least one anti-thyroid agent in one or more formulations.

2. The therapeutic method of claim 1, wherein the treatment is effective to achieve at least one of the following:
   (a) sensitization in the cancer patient to the concomitant anti-cancer therapy; and
   (b) treating the cancer.

3. The therapeutic method of claim 1, wherein said biochemical analogue is an L-isomer of $T_3$.

4. The therapeutic method of claim 3, wherein said L-isomer of $T_3$ is liothyronine sodium.

5. The therapeutic method of claim 1, wherein the cancer is a solid cancer.

6. The therapeutic method of claim 5, wherein the solid cancer is glioma.

7. The therapeutic method of claim 6, wherein the glioma is glioblastoma.

8. The therapeutic method of claim 1, wherein the anti-thyroid agent is propylthiouracil (PTU) or methimazole.

9. The therapeutic method of claim 8, wherein, when the anti-thyroid agent is methimazole, methimazole is administered in an amount between 10 mg and 80 mg per day, and when the anti-thyroid agent is PTU, PTU is administered in an amount of between 100 mg and 1200 mg per day.

* * * * *